United States Patent [19]

Morris et al.

[11] Patent Number: 4,542,117
[45] Date of Patent: Sep. 17, 1985

[54] CATALYST COMPOSITION, METHOD FOR ITS PRODUCTION

[75] Inventors: George E. Morris, Egham; Barry Nay, Woking; David G. Stewart, Epsom, all of England

[73] Assignee: The British Petroleum Company p.l.c., London, England

[21] Appl. No.: 512,740

[22] Filed: Jul. 11, 1983

[30] Foreign Application Priority Data

Jul. 14, 1982 [GB] United Kingdom ............... 8220421

[51] Int. Cl.$^4$ .................... B01J 29/06; B01J 21/08
[52] U.S. Cl. ..................... 502/66; 502/243; 502/250; 502/252
[58] Field of Search ............... 502/66, 67, 71, 77, 502/243, 250, 61, 251, 252

[56] References Cited

U.S. PATENT DOCUMENTS

| | | | |
|---|---|---|---|
| 3,755,145 | 8/1973 | Orkin | 502/67 X |
| 4,151,190 | 4/1979 | Murchison et al. | 502/243 X |
| 4,283,306 | 8/1981 | Herkes | 502/202 |
| 4,340,503 | 7/1982 | Rao et al. | 502/177 |
| 4,362,653 | 12/1982 | Robinson | 502/64 X |

*Primary Examiner*—Carl F. Dees
*Attorney, Agent, or Firm*—Brooks Haidt Haffner & Delahunty

[57] ABSTRACT

A catalyst composition for use in the production of hydrocarbons from synthesis gas comprises the essential metals (a) at least one of iron, cobalt, nickel and ruthenium, and
(b) at least one of lithium, sodium, potassium, calcium and magnesium supported on silicate, as described and claimed in U.S. Pat. No. 4,061,724, the metals [(a)+(b)] being present on the silicalite support in an amount in the range from 0.5 to 15% by weight. The catalyst composition may be modified by addition of the hydrogen form of a crystalline zeolite having the composition expressed as mole ratios of oxides:

$$0.9 \pm 0.2\ M_{2/n}O : W_2O_3 : 20\ \text{to}\ 50\ YO_2 : zH_2O$$

wherein M is at least one cation, n is the valence thereof, W is aluminum and/or gallium, Y is silicon and/or germanium and z has a value of 0 to 40, said zeolite being characterized by an XRD pattern which is substantially that of an MFI-type zeolite. Synthesis gas is converted to olefinic hydrocarbons using the unmodified catalyst and to gasoline range hydrocarbons using the modified catalyst.

9 Claims, No Drawings

CATALYST COMPOSITION, METHOD FOR ITS PRODUCTION

The present invention relates to a catalyst composition suitable for use in a process for the production of hydrocarbons from synthesis gas, to a method for its production and to its use as a catalyst in such a process.

Recent world events and a forecast longer-term shortage of oil and gas have concentrated attention on the production of gasoline range hydrocarbons from far more abundant long-term resources, such as fossil fuels, especially coal, which can be converted to a gasoline mixture comprising carbon monoxide and hydrogen (hereinafter to be referred to as synthesis gas), which in turn can be converted to hydrocarbons. A practical long-known method for effecting this conversion is the Fischer-Tropsch synthesis which employs in its simplest form a supported iron catalyst, though over the years a variety of alternative metals, such as cobalt, ruthenium, nickel and tungsten and a variety of promoters, such as thoria, potassium carbonate, potassium oxide and alumina, have been proposed. The product of such a process consists of a broad spectrum of hydrocarbons between $C_1$ and $C_{30}$ and is mainly composed of linear paraffins. The use of such a product for fuels and chemicals feedstocks requires lengthy and expensive separation procedures.

More recently, a new class of synthesis gas conversion catalysts comprising a carbon monoxide reduction catalyst combined with a ZSM-5 type zeolite developed by Mobil has been reported. It has been demonstrated that gasoline can be produced in a yield of over 60% of total hydrocarbon, constituting essentially 100% of the liquid product, by combining an iron Fischer-Tropsch catalyst with an excess volume of a ZSM-5 type zeolite. In a further development, the replacement of iron in such a catalyst by ruthenium was reported. Replacement of the ZSM-5 type zeolite by silicalite, a form of silica developed by Union Carbide having a similar structure to that of ZSM-5 zeolite, impregnated with iron and promoted by potassium is reported to have an exceptionally high selectivity for the production of $C_2$-$C_4$ olefins from synthesis gas.

We have now developed a catalyst composition having a high selectivity in the conversion of synthesis gas to hydrocarbons and in a modification thereof to gasoline range hydrocarbons, in particular aromatic hydrocarbons.

Accordingly, the present invention provides a catalyst composition suitable for use in a process for the production of hydrocarbons from synthesis gas which composition comprises the essential metals:

(a) at least one of iron, cobalt, nickel and ruthenium, and
(b) at least one of lithium, sodium, potassium, calcium and magnesium supported on silicalite, the metals [(a)+(b)] being present on the silicalite support in an amount in the range from 0.5 to 15% by weight.

As used throughout this specification, the term "silicalite" means the product as described and claimed in U.S. Pat. No. 4,061,724.

Silicalite, is a silica polymorph, which after calcination in air at 600° C. for one hour has a mean refractive index of 1.39±0.01, a specific gravity at 25° C. of 1.70±0.05 g/cc and an X-ray powder diffraction pattern in which the six strongest d-values are those set forth in Table A hereinafter.

TABLE A

| d-A | Relative Intensity |
|---|---|
| 11.1 + 0.2 | VS |
| 10.0 + 0.2 | VS |
| 3.85 + 0.07 | VS |
| 3.82 + 0.07 | S |
| 3.76 + 0.05 | S |
| 3.72 + 0.05 | S |

Silicalite may suitably be prepared by the hydrothermal crystallisation of a reaction mixture comprising water, a source of silica and an alkylonium compound at a pH of 10 to 14 to form a hydrous crystalline precursor, and subsequently calcining that precursor to decompose alkylonium moieties present therein. Further details of this process may be found in the aforesaid U.S. Pat. No. 4,061,724. The use of silica sources contaminated with alumina may lead to the incorporation of very small amounts of alumina into the silicalite, either within the framework structure and/or within the pores and/or on the surface of the crystals. It is desirable that the amount of alumina, especially that incorporated in the crystal lattice, be kept to a minimum. Because silicalite is essentially free of alumina it is substantially non-acidic and cannot be cation-exchanged.

In addition to the essential metals (a) and (b), there may also be present one or more of the metals thorium, zirconium and manganese (c).

A suitable catalyst composition comprises the metals iron, ruthenium and potassium supported on silicalite.

The active form of the catalyst is thought to comprise the essential metals in their metallic form, though it is possible that certain of the metals may be present in other forms, such as for example the oxides. Thus, whilst the elemental metals may be deposited on the silicalite support in metallic form, they are preferably deposited on the support in the form of reduceable compounds thereof and thereafter reduced.

The metals (a) and (c) may suitably be deposited on the silicalite support by impregnation with either aqueous or non-aqueous solutions of suitable reduceable compounds, eg the carbonyls, of the metals. Suitable non-aqueous solvents for the metal compounds include benzene, heptane, toluene and tetrahydrofuran. The metal (b) may suitably be deposited on the silicalite support by impregnation with an aqueous solution of a soluble compound of the metal, eg a hydroxide or a salt. Suitably the silicalite support may be impregnated first with an aqueous solution of a compound of the metal (b) and then with a non-aqueous solution of compounds of the metals (a) and and optionally (c). Alternatively, the metals (a) and optionally (c) may be added as separate solutions. Suitably, the silicalite after impregnation with the aqueous solution of the compound of the metal (b) may be dried and calcined, suitably at a temperature in the range 400° to 600° C., before further impregnation. The order of addition of the metals (a), (b) and (c) may be changed if so desired. Other methods conventionally used for depositing metals on supports, such as by precipitation from solutions of their salts, may be employed. The metal (a) may suitably be iron and ruthenium and the metal (c) may suitably be potassium. The ratio of (a) to (b) to (c) may vary over a wide range. After depositing the metals (a), optionally (b), and (c) in compound form on the silicalite, it is preferred to heat the silicalite in a reducing atmosphere, for example in a stream of a reducing gas. Typically this may be effected by heating the silicalite with the metals deposited thereon at a temperature in the range 200° to 450° C. in a stream of hydrogen for a period of from 1 to 72 hours.

The catalyst according to the invention comprising the essential metals (a) and (b) and the optional metal(s) (c) supported on silicalite is active for the conversion of synthesis gas selectively to olefinic hydrocarbons.

Accordingly, in another aspect the present invention provides a process for the conversion of synthesis gas to olefinic hydrocarbons which process comprises contacting the synthesis gas under conditions of elevated temperature with a catalyst as hereinbefore described.

Methods for preparing synthesis gas are well known in the art and usually involve the partial oxidation of a carbonaceous substance, eg coal. Alternatively, synthesis gas may be prepared, for example, by the catalytic steam reforming of methane. Although it is preferred to use substantially pure synthesis gas, the presence of such impurities as carbon dioxide and nitrogen can be tolerated. On the other hand, impurities which have a deleterious effect on the reaction should be avoided. The ratio of hydrogen to carbon monoxide in the synthesis gas may vary widely. Normally, the molar ratio of hydrogen to carbon monoxide may be in the range from 10:1 to 1:10, preferably from 5:1 to 1:5. Methods for adjusting the molar ratio of hydrogen to carbon monoxide by the so-called shift reaction are well known in the art.

The synthesis gas may suitably be contacted with the catalyst at an elevated temperature in the range 200° to 450° C., preferably from 225° to 375° C. The pressure may suitably be in the range from atmospheric to 100 bars.

The process may be operated batchwise or continuously, preferably continuously. The contact time, defined as:

$$\frac{\text{Volume of catalyst (in milliliters)}}{\text{Total volume of gas (in milliliters per second at NTP)}}$$

may suitably be in the range from 1 to 30 seconds, preferably from 1 to 10 seconds.

The catalyst may suitably be employed in the form of either a fixed bed, a fluidised bed or a moving bed.

Use of the catalyst of the present invention in the process for the production of olefins can lead to a high selectivity to lower olefins, for example ethylene, propylene and butylenes.

The catalyst composition according to the invention may suitably be modified by combination with the hydrogen form of a crystalline zeolite having the composition expressed as mole ratios of oxides:

$0.9 \pm 0.2 M_{2/n}O : W_2O_3 : 20 \text{ to } 50 \ YO_2 . zH_2O$ wherein M is at least one cation, n is the valence thereof, W is aluminium and/or gallium, Y is silicon and/or germanium and z has a value of 0 to 40, said zeolite being characterised by an XRD pattern which is substantially that of an MFI-type zeolite.

Preferably W is aluminium and Y is silicon.

The ratio of the silicalite supported portion to the hydrogen form of the crystalline zeolite portion of the modified catalyst may suitably be in the range from 10:1 to 1:10.

A preferred catalyst composition comprises the metals iron, ruthenium and potassium supported on silicalite and the hydrogen form of an MFI-type crystalline aluminosilicate.

MFI-type zeolites are defined in the Atlas of Zeolite Structure Types by W. M. Meier and D. J. Olson, published by the Structure Commission of the International Zeolite Association, 1978, in terms of their crystal structure as determined by reference to an XRD diffraction pattern.

Zeolite ZSM-5, as described and claimed in U.S. Pat. No. 3,702,886 (Mobil) has a composition and an XRD powder diffraction pattern conforming with that specified for the crystalline zeolite, which in its hydrogen ion-exchanged form constitutes the second component of the composition. Zeolite ZSM-5 may suitably be prepared by hydrothermal crystallisation of an aqueous mixture containing tetrapropyl ammonium hydroxide, sodium oxide, an oxide of aluminium or gallium, an oxide of silica or germanium and water, as described in the aforesaid U.S. Pat. No. 3,702,886. Alternatively, ZSM-5 may be prepared by the methods described in the complete specifications of UK Pat. Nos. 1,365,318 and 1,471,440 (Mobil) and 1,553,209 (ICI). Crystalline zeolites having the aforesaid chemical composition and XRD pattern may also be prepared by hydrothermal crystallisation of a mixture containing a source of alkali metal, a source of silica, a source of alumina, water and either a source of ammonium ions as described in our European patent publication No. 30811, or either a di- or trialkanolamine as described in our European patent publication No. 2900, or either monoethanolamine or monopropanolamine as described in European patent publication No. 2899. The aforesaid publications are only illustrative of the methods by which the desired crystalline zeolites may be prepared and are not in any way intended to be restrictive.

Whichever method is used to prepare the crystalline zeolite, the cation M in the as-synthesised form will invariably be an alkali metal and is usually sodium. It may be converted to the active hydrogen form by ion-exchange. Suitably ion-exchange may be effected either with an aqueous solution of an acid, for example a mineral acid, such as hydrochloric acid, or with an aqueous solution of an ammonium salt to form the ammonium-exchanged form, followed by decomposition of the ammonium-exchanged form. Such techniques are conventionally employed in the art.

It is particularly preferred to produce the modified catalytic composition for use in the process of the invention by mixing that portion of the catalyst comprising the metals (a) and (b) and optionally (c) supported on silicalite with the ammonium ion-exchanged form of the crystalline zeolite of defined composition and XRD pattern and, after mixing, decomposing the ammonium ion-exchanged form of the crystalline zeolite to produce the hydrogen form.

As mentioned hereinbefore, the modified catalyst composition of the present invention is active for the conversion of synthesis gas to gasoline range hydrocarbons and in particular to aromatic hydrocarbons.

According to another aspect of the present invention there is provided a process for the production of gasoline range hydrocarbons from synthesis gas which process comprises contacting synthesis gas at elevated temperature and either atmospheric or elevated pressure with a catalyst comprising the modified catalyst composition as hereinbefore described.

Although it is preferred to use substantially pure synthesis gas, the presence of such impurities as carbon dioxide and nitrogen can be tolerated. On the other hand, impurities which have a deleterious effect on the reaction should be avoided. The ratio of hydrogen to carbon monoxide in the synthesis gas may vary widely. Normally the molar ratio of hydrogen to carbon monoxide may be in the range from 5:1 to 1:5.

The elevated temperature may suitably be in the range from 200° to 550° C. and the pressure may suitably be in the range from 0 to 100 bars.

The process may be operated batchwise or continuously, preferably continuously. The contact time, defined as:

$$\frac{\text{Volume of catalyst in (milliliters)}}{\text{Total volume of gas (in milliliters/second at NTP)}}$$

may suitably be in the range from 1 to 30 seconds.

The catalyst may suitably be employed in the form of either a fixed bed, a fluidised bed or a moving bed. Before use in the reaction the composition is preferably activated by heating in a reducing atmosphere, for example in a stream of a reducing gas. Typically this may be effected by heating the catalyst at a temperature in the range from 200° to 450° C. in a stream of hydrogen for a period of from 1 to 72 hours.

The invention will now be particularly described by reference to the following Examples.

EXAMPLE 1

Preparation of [$Ru_{0.24}Fe_{0.3}K_{0.13}Silicalite_{6.8}$][H-MFI] Composition Using Non-Aqueous Solvent Silicalite (6.8 g) was impregnated with potassium hydroxide (0.18 g) in water (6 ml). The mixture was dried on a steam bath for 2 hours and then calcined at 440° C. in a slow stream of air for 4 hours.

$Fe_3(CO)_{12}$ (0.9 g) dissolved in tetrahydrofuran (40 ml) was added to the silicalite/KOH in six multiple incipient wetness impregnations, (6-8 ml) each time with vacuum drying between impregnations. The final vacuum drying was carried out at 100° C.

$Ru_3(CO)_{12}$ (0.5 g) dissolved in tetrahydrofuran (60 ml) was impregnated on to the silicalite/KOH/$Fe_3(CO)_{12}$ mixture using a similar technique as for the iron impregnation.

The K/Fe/Ru impregnated silicalite was transferred to a furnace tube and heated under a slow flow of hydrogen at 120° C. for 2 hours. The reduction was then carried out as follows:- 20 min. at 220° C., 2 hours at 300° C., then cooled, all under a slow flow of hydrogen.

The impregnated silicalite (6.8 g) was mixed with MFI zeolite having a silica to alumina molar ratio of 33.7:1 (ammonia form) (7.0 g) and then pressed into small pellets. The pellets were heated at 400° C. in a stream of air for 4 hours, cooled and then sieved to 8-20 mesh. The catalyst was reduced at 208° C. under a slow flow of hydrogen for 72 hours before use.

EXAMPLE 2

Use of catalyst in the conversion of synthesis gas to hydrocarbons

Synthesis gas was passed over a bed of the [$Ru_{0.24}Fe_{0.3}K_{0.13}Silicalite_{6.8}$][H-MFI] composition prepared as described in Example 1 under the following conditions and with the following results:

Conditions

Run pressure = 20 bars
Run temperature = 450° C.
Catalyst = 15 ml
Feed gas $CO:H_2$ molar ratio = 1:1
Contact time = 1.64 sec Under these reaction conditions 53.5% of the carbon monoxide fed was converted and an organic liquid product with the following composition (% w/w) was isolated:

$C_5$-$C_8$ straight chain paraffins = 17.0
Benzene = 9.7
Toluene = 28.2
Ethyl benzene = 4.3
Xylenes = 17.2
$C_9$ to $C_{11}$ aromatics = 23.6

The main reaction products were methane and carbon dioxide.

EXAMPLE 3

Preparation of [$Ru_{0.24}Fe_{0.3}K_{0.13}SILICALITE_{6.8}$] catalyst using water as solvent To a solution of ruthenium trichloride (3.36 g) in hot deionised water (50 ml) was added a solution of iron (III) nitrate (13.02 g) in hot deionised water (50 ml) followed by a solution of potassium hydroxide (2.16 g) in deionised water (50 ml). The solution was then added to silicalite (40.92 g) and the mixture shaken for 1 minute. The slurry was dried on a rotary evaporator under high vacuum, by slowly raising the temperature to 70° C. The catalyst was then heat treated in air at 120° C. for 16 hours and then reduced as follows: 2.0 hours at 125° C, 2.0 hours at 225° C. and 2.0 hours at 320° C., then cooled all undr a slow flow of hydrogen.

EXAMPLE 4

Use of catalyst of Example 3 in the conversion of synthesis gas to olefinic hydrocarbons Synthesis gas was passed over a bed of a portion of the catalyst obtained in Example 2 under the following conditions and with the following results:

Conditions

Pressure = 20 bars
Temperature = 325° C.
Period of Run = 6.0 hours
Feed $CO/H_2$ molar ratio = 1:1
Contact time = 5.02 seconds
Catalyst = 15 ml Product Selectivity %

Ethylene: 8.0
Ethane: 5.0
Propene: 16.0
Propane: 2.0
Butene: 2.0
Overall Conversion: 26%

EXAMPLE 5

Example 4 was repeated under the following conditions and with the following results:

Conditions

Pressure = 20 bars
Temperature = 380° C.
Period of Run = 2.0 hours
Feed $CO/H_2$ molar ratio = 1:1
Contact time = 2.54 seconds
Catalyst = 15 ml Product Selectivity %

Ethylene: 8.0
Ethane: 6.0
Propene: 16.0
Propane: 2.0
Butene: 1.0
Overall Conversion: 32%

Comparison Test 1

A catalyst consisting of 3.03% w/w ruthenium supported on silicalite was prepared using an abbreviated form of the procedure described in Example 2.

Synthesis gas was passed over a bed of the catalyst under the following conditions and with the following results:

Conditions

Pressure = 30 bars
Temperature = 410° C.
Period of Run = 6 hours
Feed $CO/H_2$ molar ratio = 1:1
Contact time = 0.56 seconds
Catalyst = 6 ml Product Selectivity %

Ethylene: 1.0
Ethane: 11.08
Propene: 9.06
Propane: 12.06
Overall Conversion: 47.57%

Comparative Test 2

A catalyst consisting of 15% w/w iron supported on silicalite was prepared using an abbreviated form of the procedure described in Example 2.

Synthesis gas was passed over a bed of the catalyst under the following conditions and with the following results:

Conditions

Pressure = 30 bars
Temperature = 535° C.
Period of Run = 1 hour
Feed $CO/H_2$ molar ratio = 1:1
Contact time = 0.53 seconds
Catalyst = 6 ml Product Selectivity %

Ethylene: 0.8
Ethane: 10.22
Propene: 3.98
Propane: 10.93
$C_4$: 8.36
Overall Conversion: 75.37%

EXAMPLE 6

Preparation of
[$Ru_{0.24}Fe_{0.3}K_{0.13}$SILICALITE]$_{1.3}$[H-MFI] catalyst

A further portion of the impregnated silicalite (8 g) obtained in Example 3 was mixed with the ammonium ion-exchanged form of an MFI zeolite (6.0 g) having a silica to alumina molar ratio of 33.7:1 and pressed into small pellets. The pellets were heated at 400° C. in a stream of air for 4 hours, cooled and sieved to 8–20 B.S.S. mesh. The catalyst was reduced at 225° C. under a slow flow of hydrogen for 18 hours.

EXAMPLE 7

Use of the catalyst of Example 6 in the conversion of synthesis gas to hydrocarbons Synthesis gas was passed over a bed of the catalyst obtained in Example 6 under the following conditions and with the following result:

Conditions

Run Pressure = 20 bars
Run Temperature = 394° C.
Catalyst = 15 ml
Feed $CO/H_2$ molar ratio = 1:1
Contact time = 6.39 seconds Results Under these reaction conditions 53.6% of the carbon monoxide fed was converted and an organic liquid product with the following composition (% w/w) was isolated.

$C_5$-$C_8$ straight chain paraffins: 23.1
Benzene: 4.1
Toluene: 17.3
Xylenes: 21.0
Ethyl Benzene: 4.0
$C_9$-$C_{11}$ aromatics: 30.5

We claim:

1. A catalyst composition suitable for use in a process for the production of hydrocarbons from synthesis gas which composition comprises the essential metals:
   (a) ruthenium and at least one of iron, cobalt, and nickel, and
   (b) at least one of lithium, sodium, potassium, calcium and magnesium supported on silicalite, the metals [(a)+(b)] being present on the silicalite support in an amount in the range from 0.5 to 15% by weight.

2. A catalyst composition according to claim 1 additionally incorporating one or more of the metals thorium, zirconium and manganese.

3. A catalyst composition according to claim 1 comprising the metals iron, ruthenium and potassium supported on silicalite.

4. A catalyst composition suitable for use in a process for the production of hydrocarbons from synthesis gas which composition comprises the essential metals:
   (a) ruthenium and at least one of iron, cobalt, and nickel, and
   (b) at least one of lithium, sodium, potassium, calcium and magnesium supported on silicalite, the metals [(a)+(b)] being present on the silicalite support in an amount in the range from 0.5 to 15% by weight, modified by combination with the hydrogen form of a crystalline zeolite having the composition expressed as mole ratios of oxides:

$$0.9 \pm 0.2 M_{2/n}O : W_2O_3 : 20 \text{ to } 50 \text{ } YO_2 : zH_2O$$

wherein M is at least one cation, n is the valence thereof, W is aluminium and/or gallium, Y is silicon and/or germanium and z has a value of 0 to 40, said zeolite being characterised by an XRD pattern which is substantially that of an MFI-type zeolite.

5. A modified catalyst composition according to claim 4 wherein W is aluminium and Y is silicon.

6. A modified catalyst composition according to claim 4 wherein the ratio of the silicalite supported portion to the hydrogen form of the crystalline zeolite portion is in the range from 10:1 to 1:10.

7. A modified catalyst composition according to claim 4 comprising the metals iron, ruthenium and potassium supported on silicalite and the hydrogen form of an MFI-type crystalline aluminosilicate.

8. A method for producing the modified catalyst composition as claimed in claim 4 which method comprises mixing that portion of the catalyst comprising the metals (a) and (b) and optionally (c) supported on silicalite with the ammonium ion-exchanged form of the crystalline zeolite of defined composition and XRD pattern and, after mixing, decomposing the ammonium ion-exchanged form of the crystalline zeolite to produce the hydrogen form.

9. A catalyst composition suitable for use in a process for the production of hydrocarbons from synthesis gas which composition comprises the essential metals:
  (a) iron and ruthenium, and
  (b) at least one of lithium, sodium, potassium, calcium and magnesium supported on silicalite, the metals [(a)+(b)] being present on the silicalite support in an amount in the range from 0.5 to 15% by weight.

* * * * *